(12) United States Patent
Berlendis

(10) Patent No.: US 6,427,495 B1
(45) Date of Patent: Aug. 6, 2002

(54) COMPACT MACHINE FOR THE TREATMENT OF CORD FABRICS, IN PARTICULAR FOR DYEING

(76) Inventor: Lorenzo Berlendis, Via Linneo 14, Bergamo (IT)

( * ) Notice: Subject to any disclaimer, the term of this patent is extended or adjusted under 35 U.S.C. 154(b) by 124 days.

(21) Appl. No.: 09/589,344

(22) Filed: Jun. 8, 2000

(51) Int. Cl.[7] ............................... D06B 3/26; D06B 3/28
(52) U.S. Cl. ............................................. 68/152; 68/178
(58) Field of Search .......................... 68/177, 178, 152, 68/153

(56) References Cited

FOREIGN PATENT DOCUMENTS

| DE | 1814380 | * 12/1968 | .................. 68/177 |
| FR | 2681615 | 3/1993 | |

* cited by examiner

*Primary Examiner*—Philip R. Coe
(74) *Attorney, Agent, or Firm*—Jacobson Holman, PLLC

(57) ABSTRACT

A compact machine for the treatment of cord fabrics, in particular for dyeing, is made up of a container of any shape, in one top part of which is set at least one motor-driven reel for moving the cord fabric, a device for jet-dyeing by the spraying of dye on the fabric set on at least one side of the at least one reel, and a device for overflow-dyeing of the fabric, which is set on the other side of the at least one reel, there being set underneath said at least one reel and underneath said devices a reservoir, which is designed to contain the fabric and the treatment liquid bath and which can move basically crosswise with respect to the direction of displacement of the cord fabric in order to fold the cord fabric in the reservoir itself. The displacement of the reservoir inside the container is simply crosswise in a rectilinear or oscillating fashion, or else is a motion made up of both types of motion, and the speed of the reservoir is fixed, or else variable in time.

16 Claims, 7 Drawing Sheets

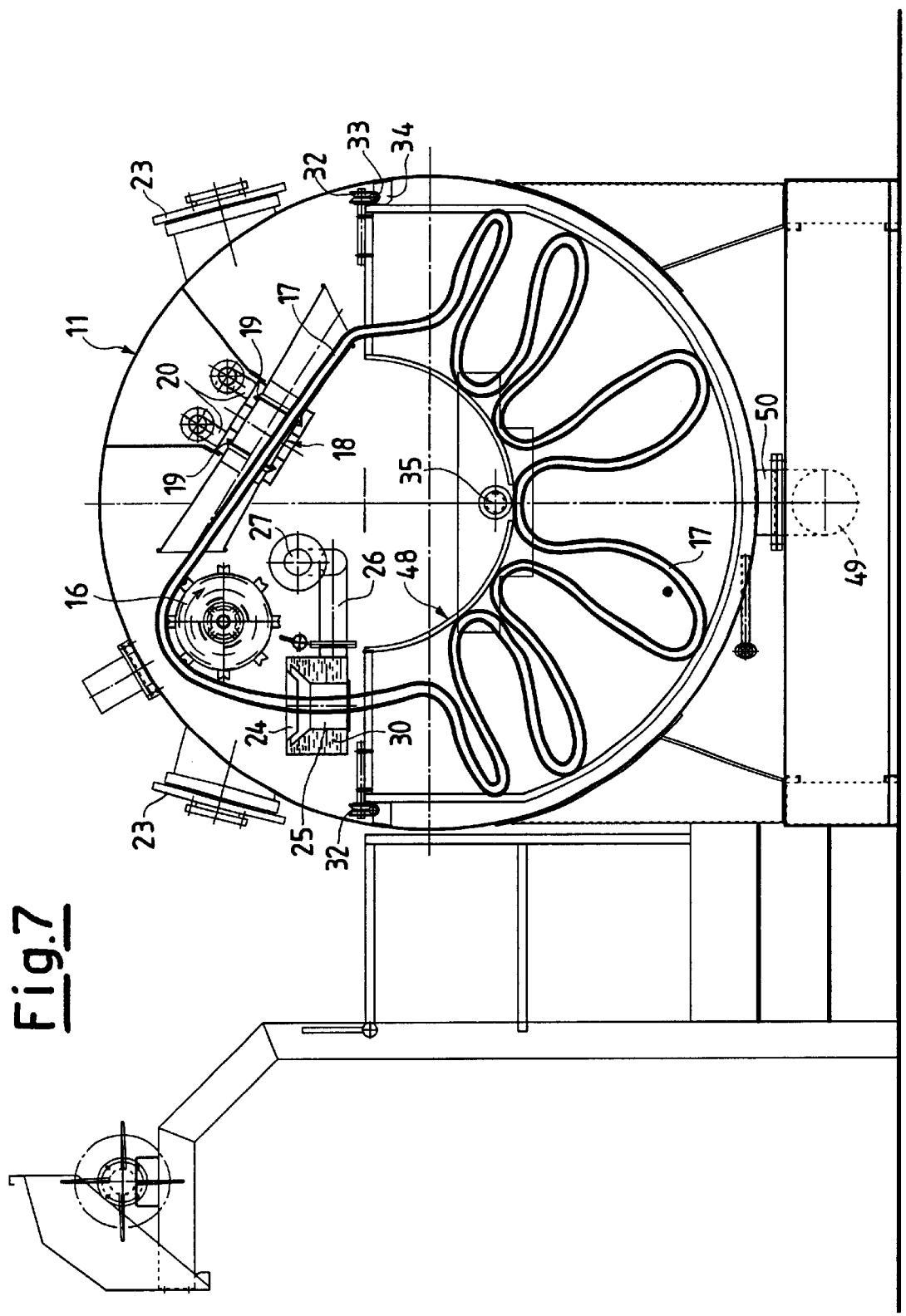

COMPACT MACHINE FOR THE TREATMENT OF CORD FABRICS, IN PARTICULAR FOR DYEING

The present invention refers to a compact machine for the treatment of cord fabrics, in particular for dyeing.

In general, these types of machines enable various processes to be carried out, such as dyeing, bleaching, and washing of fabric. The said machines are made up of a tank-type container above which is set a motor-driven reel for movement of the cord fabric and within which a reservoir is set containing the treatment liquid dye. The cord fabric set so as to form a closed loop is made to rotate inside the machine in a single direction of rotation.

Between the reel and the reservoir, nozzles are set which spray the treatment liquid at high temperature onto the fabric, which is set folded in the reservoir. The circulation of the cord fabric proceeds for a time necessary for optimization of the treatment.

It is known that a machine of this type involves considerable time for treatment and, notwithstanding this, does not enable a perfectly treated fabric to be obtained. This is due, for example, to the fact that the so-called pile of the fabric, by setting itself in a fixed direction during processing, given the single direction of rotation, enables a fabric to be obtained with a good treatment in a single direction.

It is also to be noted that in known machines this folded arrangement of the fabric is obtained by means of rod systems, which, albeit bringing about the folded arrangement of the fabric with a certain continuity, are not able to detect possible knots, tears, etc. in the fabric, and to stop the process in time.

With the said machines, it is therefore necessary to repeat the treatment after reversing the looped fabric inside the machine, with a consequent increase in processing times and costs. In addition, a lengthening of the treatment times involves replacement of the bath, or, in any case, a continuous check on the latter, with the obvious need for topping up in the case of dyeing and bleaching.

It is also known that existing machines which enable, instead, a treatment in both directions of fabric feed turn out to be particularly complicated in terms-of construction and are hence costly, even though they operate well.

A purpose of the present invention is to provide a compact machine for the treatment of cord fabrics, in particular for dyeing, which eliminates the problems concerning times and costs referred to above.

A further purpose is to provide a machine in which the folded arrangement of the fabric in the bath is optimal, without the presence of complicated mechanisms, and in which it is possible to detect any defects and discontinuities in the cord fabric being treated.

Yet another purpose is to obtain a machine which enables a considerable simplification of the component elements.

These purposes according to the present invention are achieved by providing a compact machine for the treatment of cord fabrics, in particular for dyeing, as set forth in Claim 1. Further characteristics are specified in the dependent claims.

In such a machine, a reservoir is advantageously present, which is provided with a crosswise motion with respect to the direction of feed of the fabric, which makes it possible to fold the fabric both in the case where the fabric is moved according to a clockwise rotation and in the case where it is moved according to a counter-clockwise rotation.

To achieve this, the reservoir is provided with a crosswise motion with respect to the direction of feed of the fabric, which drops vertically from the reel. The path of the reservoir may be either rectilinear or curvilinear, and its speed of motion may be either fixed or variable. The motion may be transmitted to the reservoir by means of a mechanical, hydraulic or pneumatic device.

The structural and functional characteristics and the advantages of a compact machine for the treatment of cord fabrics according to the present invention may be better understood from the ensuing description, which is given to provide a non-limiting example, with reference to the schematic drawings attached, in which:

FIG. 7 is a section of a fourth example of embodiment of a machine according to the invention, in which the single reel is set inside the container.

Figure 1:
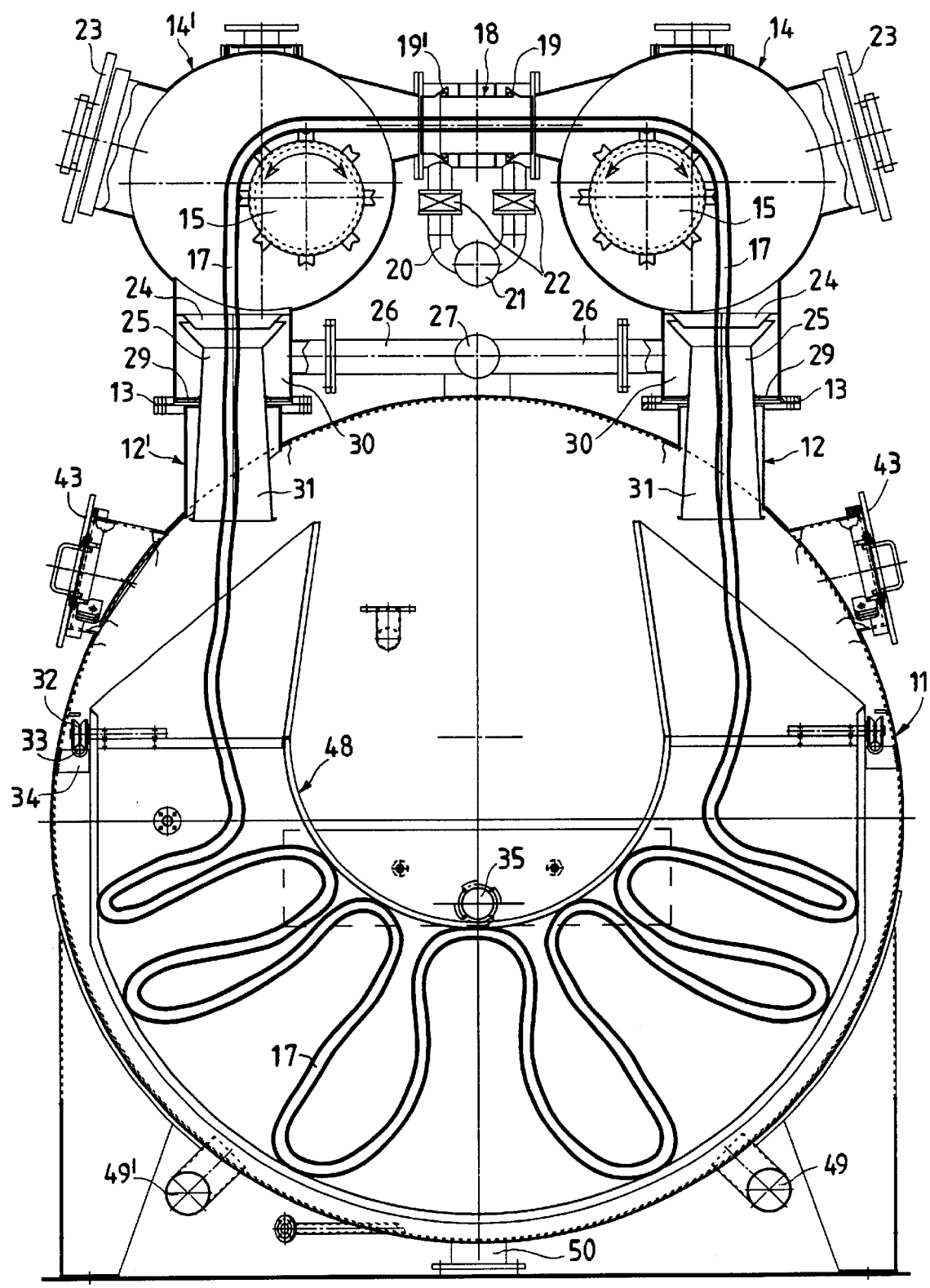
FIG. 1 is a cross section of a first example of a machine according to the invention taken along the trace I—I of FIG. 2, in which the reels are set above the container.
Figure 2:
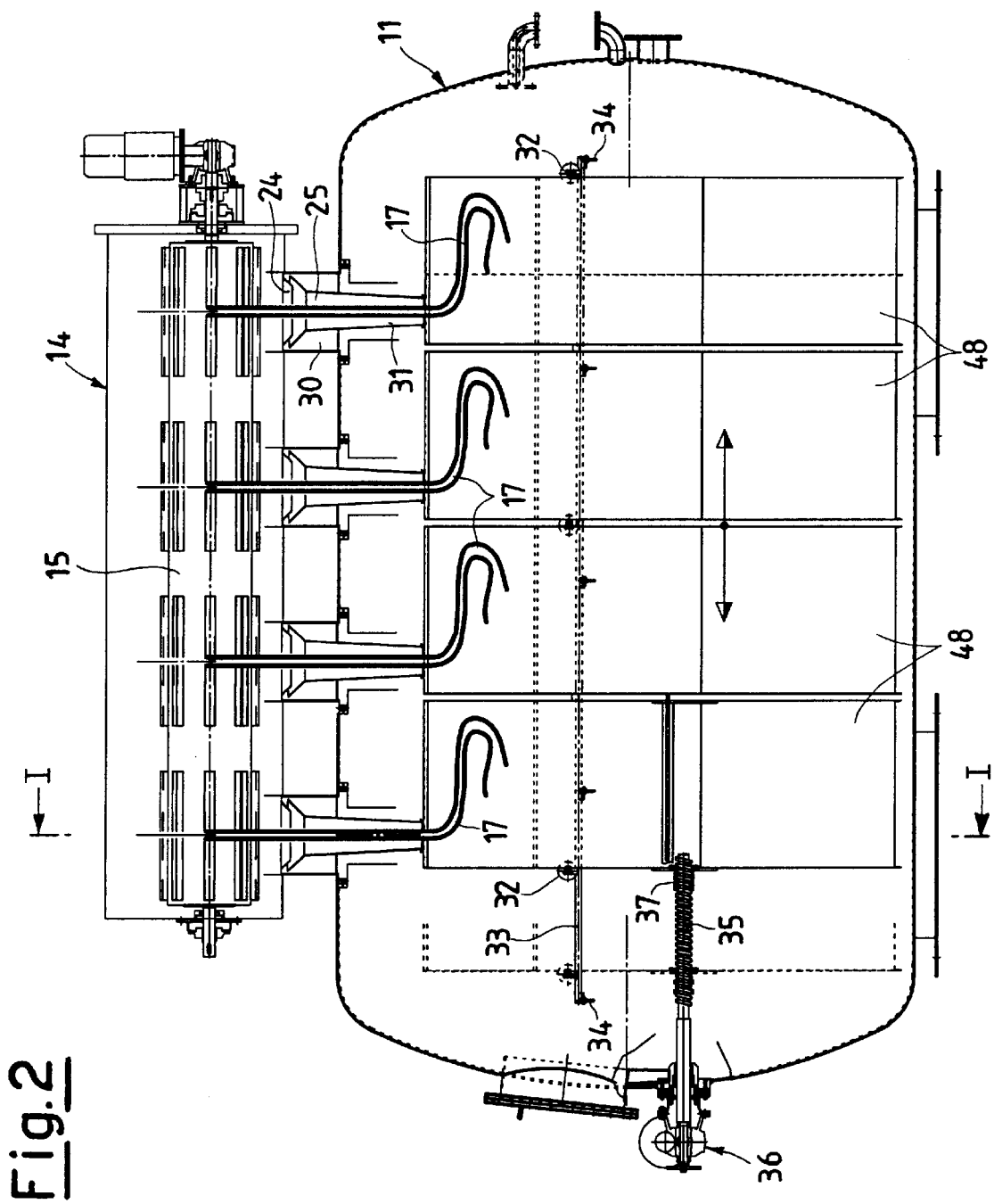
FIG. 2 is a longitudinal section of a machine similar to the one illustrated in FIG. 1, in which a number of turrets are provided that contain the reels and are set above the container.
Figure 3:
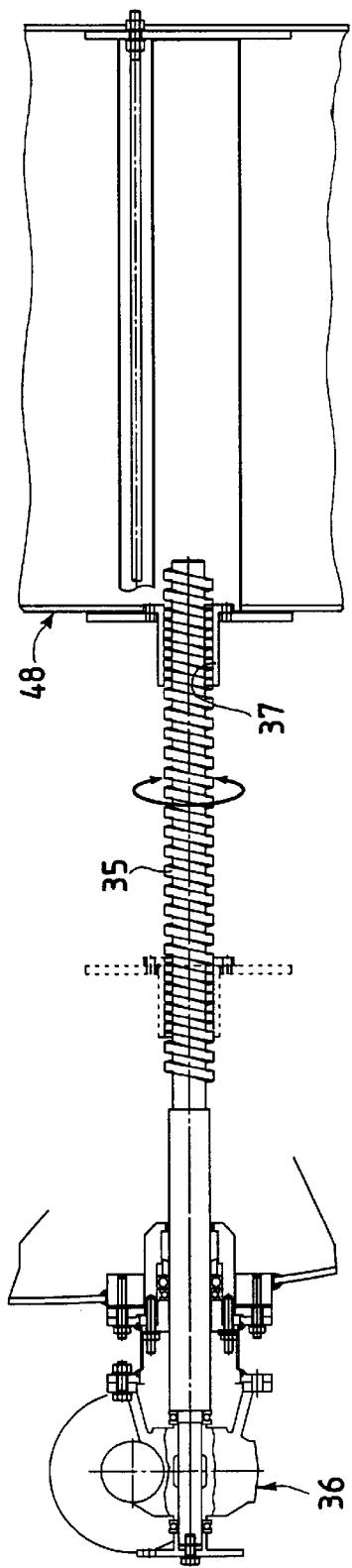
FIG. 3 is an enlarged detail of FIG. 2 illustrating a device for the crosswise movement of the bath to fold the fabric.

With reference first to FIGS. 1–3, a first example of a compact machine for the treatment of cord fabrics, made according to the invention and in particular used for dyeing, is presented. However, the same machine may be used also for other types of treatment, such as bleaching, washing and the like.

The machine is made up of a tank-type container 11, the top part of which extends in two protruding separate portions 12, 12' of a tubular type, in which two towers 14, 14' set alongside one another are arranged by means of flanges 13. The said towers 14, 14', which are of a basically cylindrical shape, each contain one reel 15. The reels 15 are motor-driven in both directions of rotation for feeding cord fabric 17, which is wound so as to form a closed loop, and are connected together by a pipe 18 equipped with two nozzles 19 and 19' to form a so-called "jet pipe".

The nozzles 19 and 19' subject the fabric 17 to the action of spraying of treatment liquid at high temperature. The nozzles 19 and 19' in fact are divided into two sets which operate according to the direction of translation of the fabric 17 inside the pipe 18 and are selectively fed by respective pipes 20, which come from a central manifold 21 supplied by a pump (not shown) and are equipped with closing valves 22. The towers 14, 14' are moreover provided, on their sides, with inspection doors 23 which can be freely opened for arranging the cord fabric 17 that passes inside the machine. Doors 43 are also provided in the tank container 11 to facilitate arrangement of the fabric. Underneath each of the towers 14, 14', within the protruding portions 12, 12' of the tank container 11, conveying cones 24 and 25 are set which are in line one after the other and are tapered downwards. The cones 25 are moreover detached beneath the first cones 24 and are each provided with a cylindrical portion which extends downwards supported by an external closing wall 29 within the protruding portions 12, 12', so as to identify chambers 30. It is to be noted how, inside the said chambers 30, the treatment-bath liquid is introduced, fed in by a pair of pipes 26 which come from a common central manifold 27. As a result of the transfer, the bath liquid passes within the cones 25, impregnating the cord fabric 17.

The free end of each second cone 25 is aligned with a length of pipe 31, which has, towards its bottom end, a cross section shaped like an ellipse or a flattened circle, in a plane which is longitudinal with respect to the machine, and is designed to convey the fabric into an underlying reservoir 48 set in the tank container 11. In the bottom part of the tank container 11, a reservoir 48 is in fact provided according to the invention, the said reservoir having a hollow U shape extending for a dimension beyond a half-circumference of the container itself The reservoir 48 moves inside the container 11 with a motion that enables the fabric in the reservoir itself to be folded. A possible arrangement that enables reciprocating actuation of displacement of the reservoir 48 is illustrated in FIG. 3 and consists of a worm screw 35, driven at one end by a motor reducer 36, which is located on the container 11. The worm screw 35 engages an internal thread 37 which is fixed to an outer central area and is located above the reservoir 48. In this way, operation of the worm screw 35 determines displacement of the reservoir 48 according to a reciprocating motion.

In this connection it should be noted that on the reservoir 48, at least laterally, wheels 32 are fixed on opposite sides, the said wheels running on two guides 33 which are fixed to the container 11 by means of a support 34.

Thanks to the above arrangement, the reservoir 48 is suspended inside the container 11 in such a way that it can be displaced inside the latter. It is evident that the oscillating or to-and-fro movement of the reservoir 48 can equally be obtained by means of a pneumatic or hydraulic cylinder actuator, or by means of a direct motor reducer, with possible adjustment of their motion.

On the bottom of the reservoir 48 a pair of suction openings 49, 49' are provided, which are set on opposite sides of the container 11 and are connected to a bath-circulation pump (not illustrated). Also a pipe 50 of the container for maintenance or discharge of the bath is provided at the centre.

Figure 4:
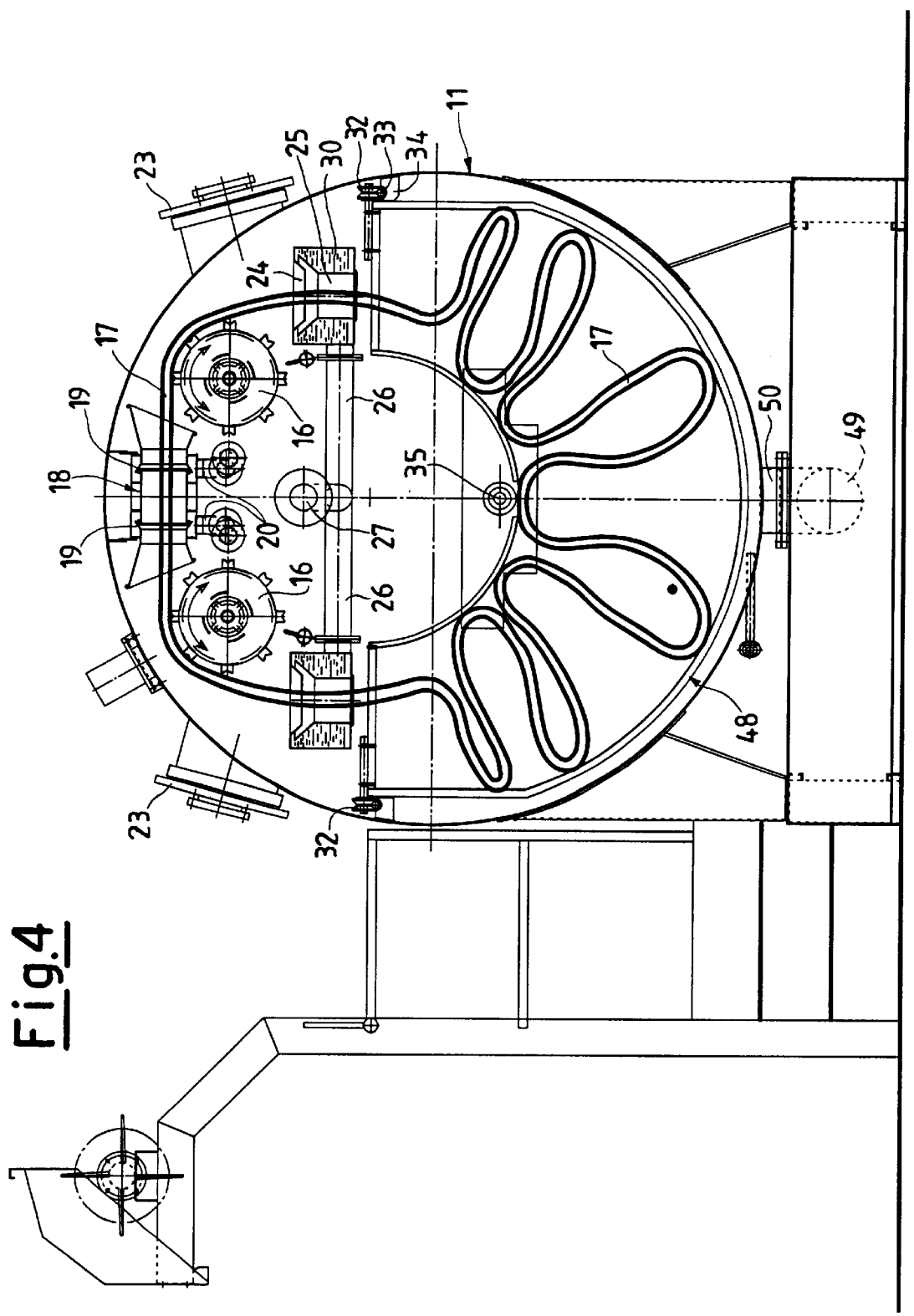
FIGS. 4 and 5 are schematic views of a second embodiment of a machine similar to that of FIGS. 1 and 2, in which the reels are set inside the container, and the movement device is similar to that of FIG. 3.
Figure 5:
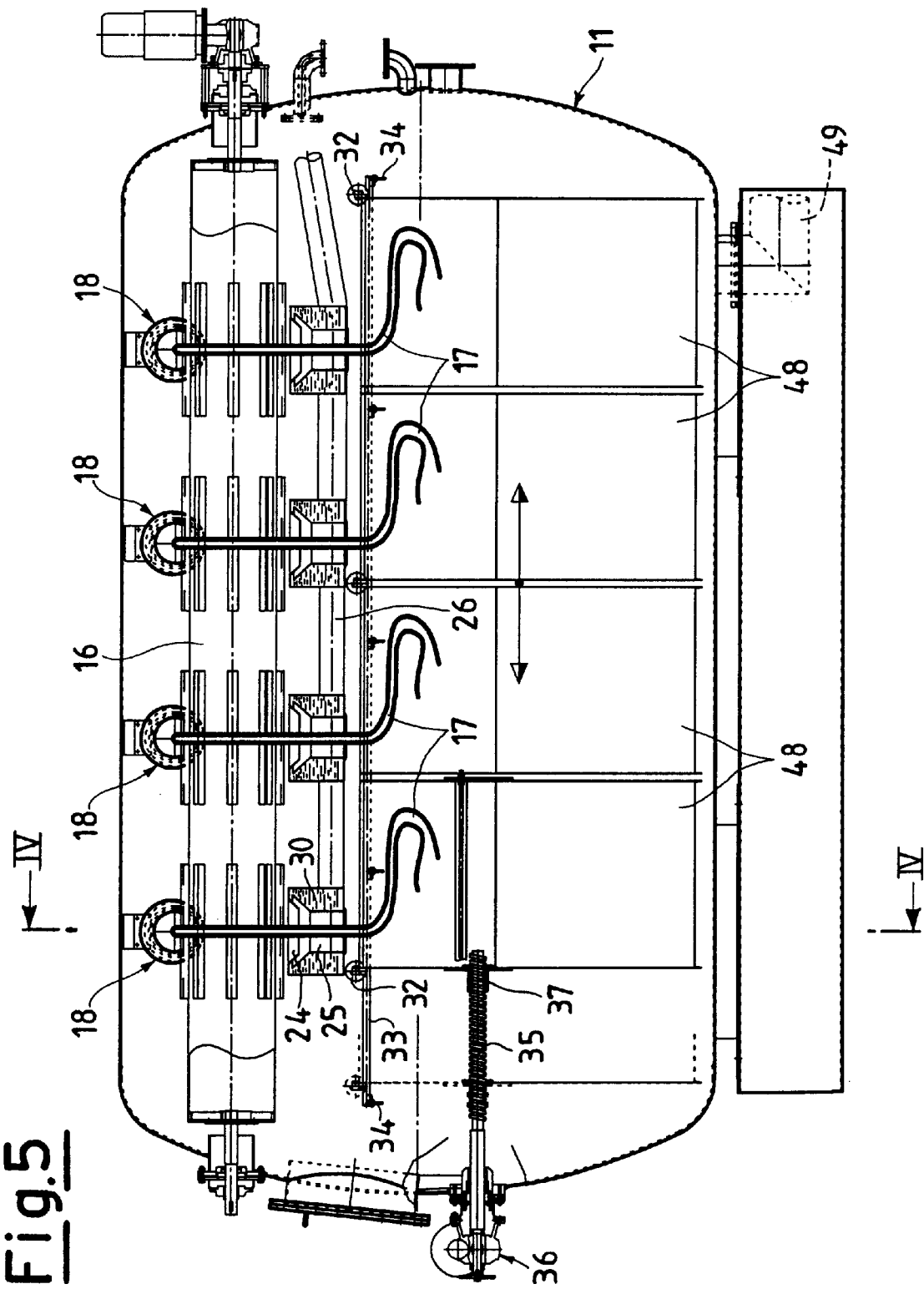

FIGS. 4 and 5 show a second example of embodiment of a machine according to the invention, in which a pair of reels 16 is set inside the container 11. This is a machine consisting of a tank-like container 11, the top part of which directly contains a pair of reels 16, the reels being motor-driven in both directions of rotation, for feeding the cord fabric 17, which is wound in closed-loop fashion. As in the previous example, between the reels 16 a pipe 18 is set which is provided with two nozzles 19 and 19' and makes up a so-called "jet pipe". The nozzles 19 and 19' spray treatment liquid at high temperature on the fabric. In points corresponding to the reels 16, at the sides of the container 11, two inspection doors 23 are provided, which can be freely opened for arranging the cord fabric 17 that passes inside the machine. Beneath each one of the two reels 16, conveying cones 24 and 25 are set which are aligned one after the other and are tapered towards the bottom; they are each contained in a box that identifies a chamber 30. The cones 25 are moreover detached beneath the first cones 24 and are each provided with a cylindrical portion which extends downwards and which, together with the walls of the containing box, defines the above-mentioned chamber 30.

It is to be noted how, inside the said chambers 30, the treatment-bath liquid is introduced, fed in by a pair of pipes 26 which come from a common central manifold 27. As a result of the transfer, the bath liquid passes within the cones 25, impregnating the cord fabric 17. The free ends of the cones 25 have the function of conveying the fabric into a reservoir 48 of the underlying tank 11.

In the bottom part of the tank container 11, a reservoir 48 is in fact provided, the said reservoir being U-shaped or circular and extending beyond a half-circumference of the container 11 itself. Motion is imparted to the reservoir 48, which moves in a basically crosswise direction with respect to the direction of feed of the fabric, inside the container 11. This enables the fabric 17 to be folded inside the reservoir 48.

As in the previous example, actuation of the reservoir 48 is the same as that illustrated in FIG. 3, and the reader is referred to that description, the reference numbers being understood to be the same.

In the examples described and illustrated so far, the machine consists of a single container 11 and a single reservoir 48, but, as shown in FIGS. 2 and 5, machines having a number of reservoirs 48 may be built. These reservoirs 48 are set alongside one another and are fixed to one another inside a single large container 11, are provided with the same motion, and are able to treat even a number of cord fabrics simultaneously. In this way, for example, using the same circulation pump the bath is unified for all the reservoirs 48, thus making possible a considerable saving in cost and a uniformity of treatment of the various cord fabrics wound in loop fashion that are treated in the machine.

Figure 6:
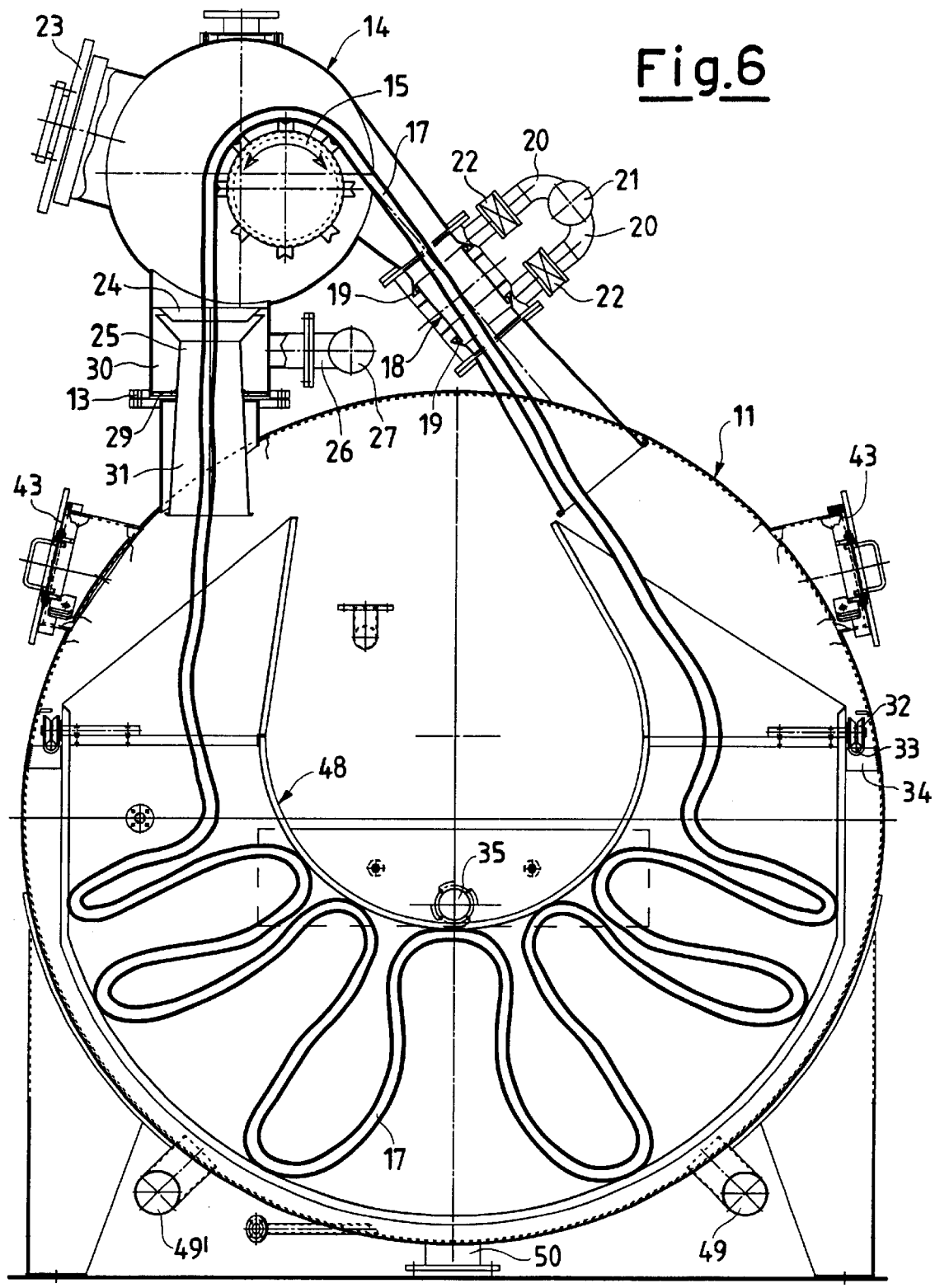
FIG. 6 is a section of a third example of embodiment of a machine according to the invention, in which there is a single reel set above and outside of the container.

FIGS. 6 and 7 show how machines according to the invention may be made with a single reel 15 or 16 set in a tower 14, or else directly inside the container. In any case, the invention envisages that the mobile reservoir 48 should be set beneath the reel with respect to the feed of the fabric 17.

In the said embodiment with a single reel 15 or 16, preferably the circulation of the fabric 17 is in a single direction.

In these arrangements with a single reel, the pipe 18 provided with two nozzles 19 and 19', which makes up the "jet pipe", has also the function of deflecting the fabric away from the reel towards the opposite end of the underlying reservoir 48. For this purpose, the pipe is set inclined between the output of the reel 15 or 16 set above one end of the reservoir and the input in the opposite end of the reservoir 48.

It is moreover possible, both in the case of reels set inside the container and in the case of reels set outside the container, to make distinct machines, each having one or more reservoirs, which are connected together so that they can work together and carry out the same type of process, or which are separate, and hence can carry out different processes. This enables optimization of production according to the batches to be processed.

Figure 8:
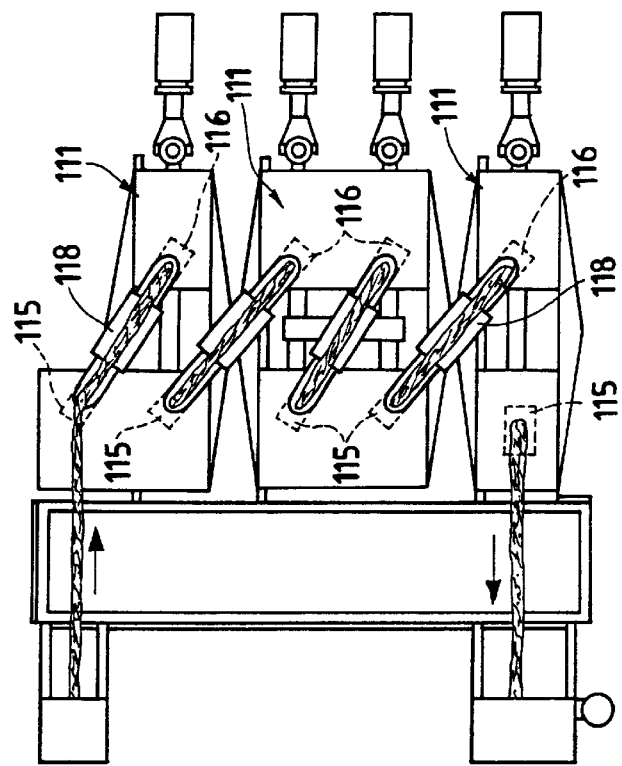
FIG. 8 shows a top plan view of a multiple machine according to the invention.

FIG. 8 shows how a multiple machine may be built in which it is possible to treat a fabric 117 in the closed loop form or otherwise with different liquids or baths. Also in this case, rotation of the fabric may be in the clockwise direction or in the counter-clockwise direction. In fact, a set of tank containers 111 contain pairs of reels 115 and 116 which are alternately connected by means of pipes 118 which crisscross between one container and another and enable continuous circulation of the fabric. The ends of composite machines may be separate, so that it is possible to treat a cord fabric the ends of which are open, or else may be connected so as to treat cord fabric of considerable length but closed in loop fashion. The individual containers may contain different types of baths or the same type of bath and are thus able to perform any type of treatment.

There follows a brief description of the operation of the machine according to the present invention.

In a first treatment step, for example dyeing, the cord fabric 17 is fed into the machine via the doors 23 and 43 and is closed in a loop fashion. Then, for example, the said fabric 17 is treated in the clockwise direction. In this first step, the fabric 17 is conveyed by the reels 15 or 16, which are made to turn in the clockwise direction, into the pipe 18 where the set of nozzles 19 is operated, which carries out a first forced treatment of the fabric with bath liquid. Next, the fabric 17, by means of the second reel 15 or 16, is sent on within the first cone 24 and then within the second, underlying, cone 25. In this phase, the bath liquid present in the chamber 30, by its transfer inside the cone 25, subjects the fabric to a second impregnation. During treatment of the fabric in the clockwise direction, the reservoir 48 set inside the container 11 containing the liquid bath is moving, so that the cord fabric 17, dropping vertically, is folded in the reservoir itself, as may be clearly seen in FIGS. 2 and 5.

In this phase the dye is aspirated and made to circulate inside the machine through the lateral or central suction opening 49 set at the bottom of the container of the machine, so as to favour feeding of the fabric inside the reservoir 48.

Then the fabric 17 goes back up passing inside the other two cones 25 and 24. During this passage, it receives a fourth and a fifth impregnation in countercurrent by means of the bath liquid present in the other chamber 30 which is transferred from the cone 25. This treatment consisting of the various impregnation steps referred to above proceeds for a pre-set time which is controlled by a central electronic equipment (not shown).

Subsequently, the electronic equipment operates the motor means that drive the reels 15 or 16 in the opposite direction, namely counter-clockwise.

The treatment is thus repeated with the sole difference that both the set 19' of nozzles present in the pipe 18 and the suction opening 49' or 49 present in the container 11 are actuated, so as to favour treatment and circulation of the fabric. Also in this case, the treatment continues for a pre-set time.

By means of a machine according to the invention it is therefore possible to treat cord fabric according to a plurality of operating steps in which the fabric is made to circulate in opposite directions automatically, without any need for intervention. The pipes 20 and 26 which are suitably sized and feed the liquid bath inside the pipes 18, as well as the chambers 30, enable simultaneous operation of these devices with differentiated flow rates of liquid, thus facilitating treatment of the fabric.

The movement of the reservoir 48 enables optimal arrangement and circulation of the fabric inside the machine. The advantageous provision of a reciprocating motion imparted to the cord fabric inside the machine according to the invention makes possible a considerable reduction in processing times and in production costs, as well as in the amount of treatment liquid bath used.

All this moreover means better and more uniform processing of the fabric, which, undergoing a surface treatment in opposite directions, is processed both with the pile and against the pile.

The fabric 17 may drop directly vertically and is not pulled, as, instead, happens when it comes into contact with special folding devices. The absence of contact moreover prevents any possible stretching of the fabric undergoing treatment.

FIGS. 6 and 7 show further variants of the invention consisting of machines, each of which is made up of a tank container, above or inside which a single reel is set, the reel being motor-driven for feeding the cord fabric; a reservoir 48 containing the treatment liquid bath is in any case set inside the container. Also this, simpler, embodiment envisages crosswise movement of the reservoir with respect to the direction of feed of the fabric, so that the fabric will be set folded inside the reservoir as it drops vertically from the reel.

In any case, the path of the reservoir may be either rectilinear, as in the examples given, or curvilinear, governed by special actuators, and its speed may be either fixed or variable. Variation in the speed of movement of the reservoir enables different types of folding of the fabric to be obtained, if the fabric proceeds at a fixed rate. Likewise, it is alternatively possible to have a fixed speed of translation of the reservoir, and the variation in the rate of feed of the fabric determines a variation in the length of the folds of the fabric in the reservoir.

Motion may be transmitted to the tank by means of any type of actuator or motor device, whether mechanical, hydraulic, or pneumatic.

What is claimed is:

1. A machine for the treatment of cord fabrics, said machine comprising: a tank containing a treatment liquid bath and at least one motor-driven reel for moving the cord fabric, said reel being set in a top part of said tank, spraying nozzles for treating the cord fabric as the cord fabric is made to pass between the spraying nozzles, a reservoir located in a vicinity of a bottom of the tank and said reservoir being movable by a corresponding actuator so that said reservoir moves in a crosswise direction with respect to a direction of feed of the cord fabric, movement of said reservoir inside said tank enabling folding of the cord fabric in the reservoir.

2. The machine according to claim 1, wherein said reservoir has a shape of a hollowed "U".

3. The machine according to claim 2, wherein said reservoir extends for a dimension beyond a half-circumference of said tank.

4. The machine according to claim 1, wherein said reservoir has a circular shape.

5. The machine according to claim 4, wherein said reservoir extends for a dimension beyond a half-circumference of said tank.

6. The machine according to claim 1, wherein two motor-driven reels are set above said reservoir, and at a top and inside of said tank.

7. The machine according to claim 5, wherein said reels are driven so that said reels rotate in a clockwise or counter-clockwise direction to move the cord fabric.

8. The machine according to claim 6, wherein said two reels are set inside two towers above said tank.

9. A machine according to claim 1, characterized in that it is provided with two motor-driven reels, set above said reservoir, and at the top and outside of said tank.

10. The machine according to claim 1, wherein said spraying nozzles are located in a pipe.

11. The machine for the treatment of cord fabrics according to claim 10, further comprising a plurality of tanks set alongside one another and connected together at points corresponding to reels set in criss-cross fashion and on opposite sides by a set of said pipes containing sets of said spraying nozzles.

12. The machine according to claim 1, wherein the cord fabric is also made to pass inside at least one chamber for impregnation with treatment liquid.

13. The machine according to claim 12, wherein said chamber comprises two conveying cones, which are set aligned in succession, detached from one another, and are contained at least partially inside a cylindrical portion which is provided at a bottom of the chamber with a closing wall.

14. The machine according to claim 1, wherein said reservoir is mobile according to a rectilinear or curvilinear path.

15. The machine according to claim 1, wherein said reservoir is mobile at a fixed speed or at a variable speed.

16. The machine according to claim 1, wherein inspection doors are provided on sides of said tank.

* * * * *